(12) United States Patent
Stearns et al.

(10) Patent No.: US 7,442,902 B2
(45) Date of Patent: Oct. 28, 2008

(54) ADAPTIVE TEMPERATURE CONTROLLER

(75) Inventors: Stanley D. Stearns, Gig Harbor, WA (US); Huamin Cai, Houston, TX (US); Chris S. Cowles, Houston, TX (US)

(73) Assignee: Valco Instruments Co., Inc., Houston, TX (US)

( * ) Notice: Subject to any disclaimer, the term of this patent is extended or adjusted under 35 U.S.C. 154(b) by 0 days.

(21) Appl. No.: 11/685,325

(22) Filed: Mar. 13, 2007

(65) Prior Publication Data
US 2007/0210285 A1    Sep. 13, 2007

Related U.S. Application Data (60) Provisional application No. 60/767,236, filed on Mar. 13, 2006.

(51) Int. Cl.
*H05B 1/02* (2006.01)
(52) U.S. Cl. .............. 219/490; 219/497; 219/505; 338/22 R; 374/1; 374/100
(58) Field of Classification Search ............... 219/490, 219/494, 497, 499, 501, 504, 505; 338/22 R, 338/22 SC; 374/1, 100, 102
See application file for complete search history.

(56) References Cited

U.S. PATENT DOCUMENTS

| | | | |
|---|---|---|---|
| 5,105,067 A * | 4/1992 | Brekkestran et al. | 219/497 |
| 5,755,670 A * | 5/1998 | McKown et al. | 600/505 |
| 5,793,022 A * | 8/1998 | Klinck et al. | 219/483 |
| 6,252,209 B1 * | 6/2001 | Liepold | 219/501 |
| 6,519,546 B1 * | 2/2003 | Eryurek et al. | 702/130 |

OTHER PUBLICATIONS

Mark H. Paschall, International Search Report - PCT/US07/63861, Aug. 7, 2008, 2 pages, United States Patent and Trademark Office as International Search Authority, Alexandria, Virginia US.

Mark H. Paschall, Written Opinion - PCT/US07/63861, Aug. 7, 2008, 2 pages, United States Patent and Trademark Office as International Search Authority, Alexandria, Virginia US.

* cited by examiner

*Primary Examiner*—Mark H Paschall
(74) *Attorney, Agent, or Firm*—James E. Hudson, III; Crain, Caton & James, P.C.

(57) ABSTRACT

The adaptive temperature controller includes an ambient temperature sensor, a device for measuring resistance, an electrically-conductive material, a power supply, and a device for controlling power. In operation, the controller determines the resistance of material at or near ambient temperature. Based on such determination so long as voltage and power are known, the resistance of the material, and therefore its instant temperature is known. Additionally, the adaptive temperature controller determines the responsiveness of the electrically-conductive material to determine the predicted increase in temperature and rate of increase in temperature relative to increases in voltage, current or power. As a result the voltage or power may be instantly varied to produce near infinite control over material temperature.

9 Claims, 5 Drawing Sheets

ADAPTIVE TEMPERATURE CONTROLLER

CROSS REFERENCE TO RELATED APPLICATIONS

This application claims the benefit of U.S. Provisional Patent Application No. 60/767,236 entitled, "Adaptive Temperature Controller" filed on Mar. 13, 2006 in the United States Patent and Trademark Office.

STATEMENT REGARDING FEDERALLY SPONSORED RESEARCH OR DEVELOPMENT

Not Applicable.

BACKGROUND OF THE INVENTION

1. Field of the Invention

This invention pertains to a device for simultaneously controlling the temperature of a heating element and monitoring its temperature. In particular, the device pertains to controlling the temperature of a heating element for use in chromatographic analysis including heating of columns, detectors and other components, although it may be used in any system wherein precise heating through a range of temperatures is desired.

2. Description of the Related Art

An adaptive temperature controller for use with any electrically-conductive material is disclosed. It is often necessary to maintain portions of test equipment or other items above ambient temperature. This has been accomplished in the prior art with various temperature controllers. It is well known to provide a source of heat that is easily controlled. Most often heat is transferred from a conductive element. In the prior art the temperature of such conductive element was monitored by a separate device, often a Resistance Temperature Detector (RTD). However this requires multiple parts, increasing the space consumed by such equipment, the weight of such equipment, and its cost. Additionally, such systems often were unable to produce rapid temperature changes. Moreover, heating of equipment was not uniform and often was not sufficiently fast.

It would therefore be a desirable improvement to have a temperature controller with fewer parts that likely would reduce weight, space and cost, would provide uniform heating, and would be capable of rapid heating and cooling.

SUMMARY OF THE INVENTION

The adaptive temperature controller disclosed herein includes a temperature sensor, a device for measuring resistance, an electrically-conductive material, and a power supply. In operation, the controller determines the resistance of the electrically-conductive material at ambient temperature and is able to determine the corresponding resistance of the electrically-conductive material at temperatures within a temperature range and to apply the voltage or current necessary to obtain such resistance. The temperature of the electrically-conductive material may be determined by using a temperature sensor or by approximation based on ambient air temperature. As a result, the voltage or power may be instantly varied to produce near infinite control over material temperature.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only typical preferred embodiments of the invention and are therefore not to be considered limiting of its scope as the invention may admit to other equally effective embodiments.

DETAILED DESCRIPTION OF THE PREFERRED EMBODIMENT

Figure 1A:
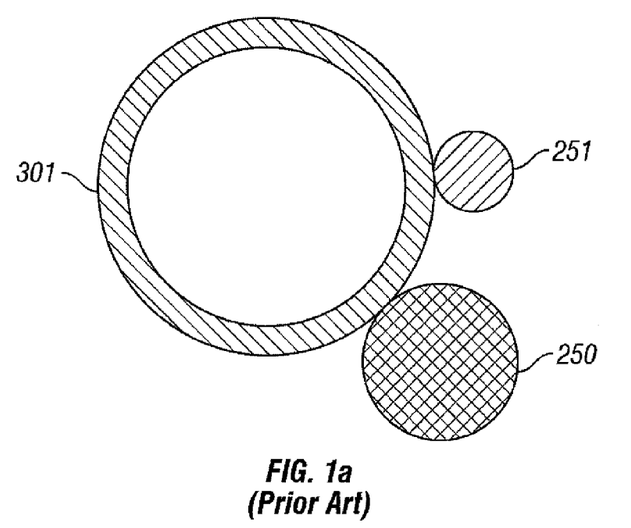
FIG. 1a depicts a cross-sectional view of one embodiment of the prior art.
Figure 1B:
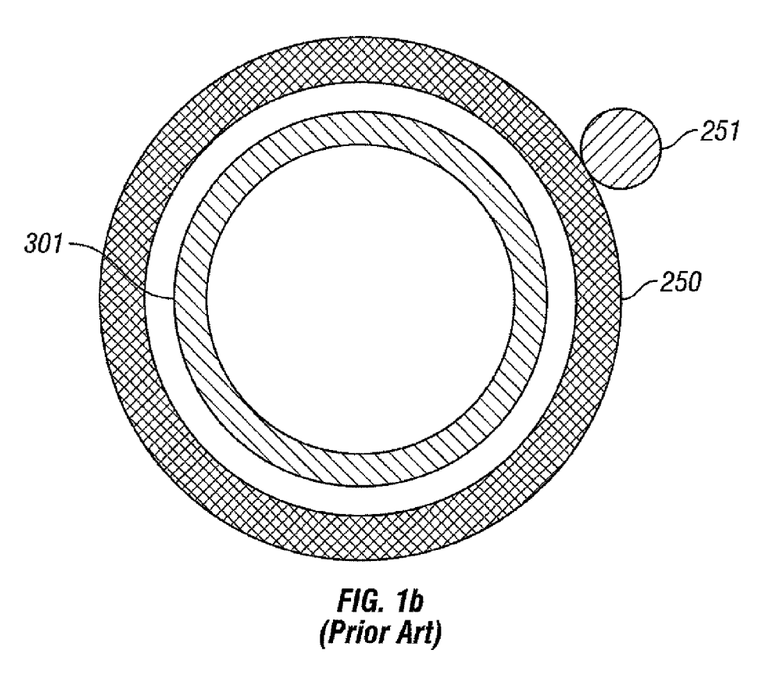
FIG. 1b depicts a cross-sectional view of another embodiment of the prior art.

As depicted in FIGS. 1a and 1b, temperature controllers are known where a conductive element 250 and a sensor 251 were placed in proximity to or about the component 301 of a system 300 to respectively heat and monitor the temperature of element 301. It is well known to provide a source of heat that is easily controlled. Most often heat is transferred from a conductive element 250 to be subsequently distributed to element 301. The conductive element 250 may be placed adjacent (FIG. 1a) or surrounding (FIG. 1b) element 301. In the prior art the temperature of conductive element 250 was monitored by a separate sensor 251, often a RTD. This requires multiple parts, increasing the space consumed by such equipment, the weight of such equipment, and its cost.

An electrically-conductive material 50 may be used to heat a component 101 of a system 100, such as a detector or column in the case of chromatographic analysis, directly or indirectly. In the case of chromatographic analysis, the component 101 may be a chromatographic column 102 of chromatographic system 100, which includes an analyte injector 103 and a detector 104. In direct heating, depicted in FIG. 2a, the component 101, a column, of the system 100 is composed, at least in part, of electrically-conductive material 50, shown in cross-section in FIG. 2b. In indirect heating, depicted in FIG. 3a, the component 101 of the system 100 is contacted by electrically conductive material 50, shown in cross section in FIG. 3b. In indirect heating, the component 101 contacted or encircled may be a detector, a column, or other device. In FIG. 3a, component 101 is again a column. The temperature to which the electrically-conductive material 50 heats the element, the rate of heating, and the duration of heating at any temperatures, is controlled by adaptive temperature controller 10. In alternative embodiments, the adaptive temperature controller may be used in conjunction with any system wherein precise temperature control throughout a range is desired.

Figures 2A, 2B:
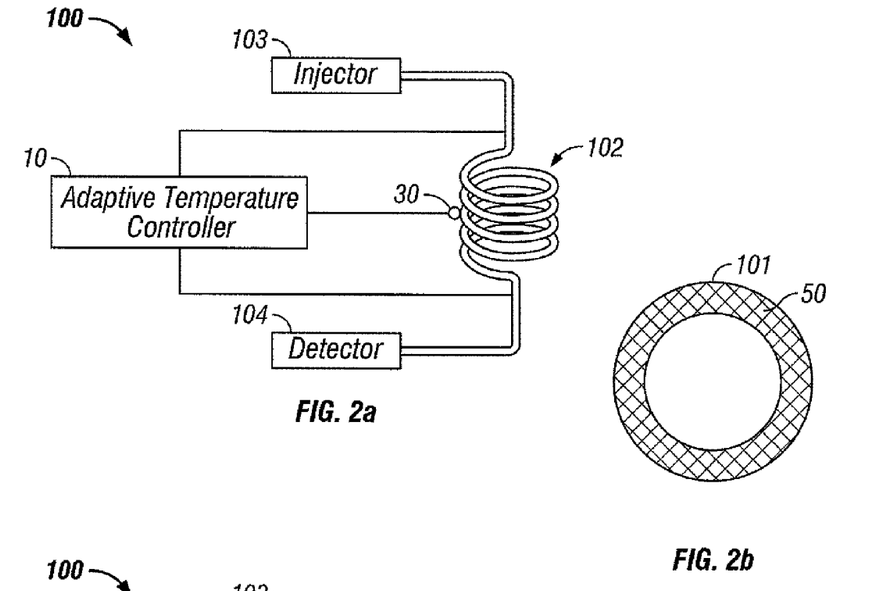
FIG. 2a depicts direct heating of the component by the adaptive temperature controller.
FIG. 2b depicts the component heated by direct heating controlled by the adaptive temperature controller.
Figure 3A:
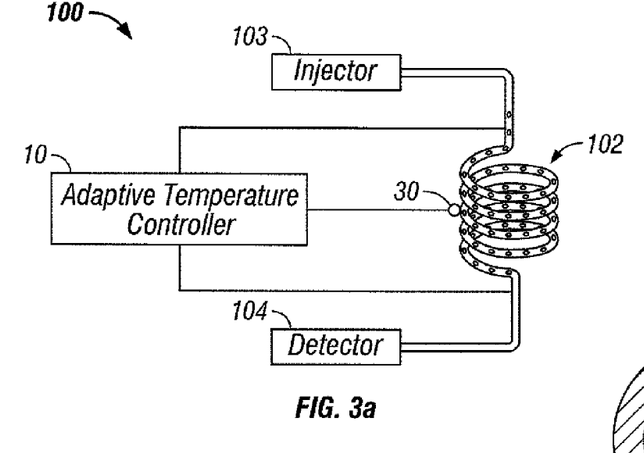
FIG. 3a depicts indirect heating of the component by the adaptive temperature controller.
Figure 3B:
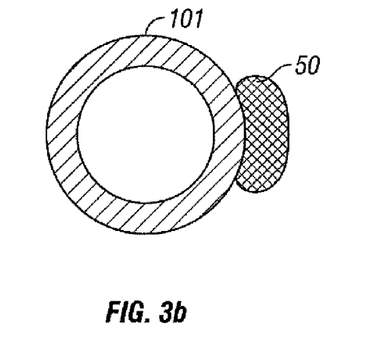
FIG. 3b depicts the component heated by indirect heating controlled by the adaptive temperature controller.

As depicted in FIGS. 2a and 3a, in operation, the electrically-conductive material 50 used in conjunction with adaptive temperature controller 10 has a known electrical resistance as a function of temperature. Adaptive temperature controller 10 is in electrically conductive communication with electrically-conductive material 50. The relationship between resistance and temperature for electrically-conductive material 50 may be obtained by adaptive temperature controller 10 by application of an equation or by interpolation from a table of such data. Since the electrical resistance of an electrically-conductive material 50 is known as a function of temperature, the temperature of the electrically-conductive material 50 can be determined by a dynamic measurement of the electrical resistance of electrically-conductive material 50. As described below, the temperature of the electrically-conductive material 50 may be determined by contact with a temperature sensor 30 or by approximation based on the ambient air temperature determined from temperature sensor 30. The temperature of electrically-conductive material 50 may therefore be controlled by virtue of the current (or voltage or both) applied to electrically-conductive material 50. In the preferred embodiment, electrically-conductive material 50 is nickel.

In instances when the resistance of the electrically-conductive material 50 is not immediately known, but its normalized resistance characteristic is known, such as in the case of an unknown length or diameter of nickel wire, the adaptive temperature controller 10 may be calibrated for use with electrically-conductive material 50 by measurement of the resistance of electrically-conductive material 50 while measuring the corresponding temperature of electrically-conductive material 50 by a temperature sensor 30. The scale factor derived by dividing the measured resistance value of electrically-conductive material 50 by the normalized resistance value of the material from which electrically-conductive material 50 is composed at the reference temperature may then be applied to the normalized resistance characteristic to determine the resistance of electrically-conductive material 50 at any particular temperature.

Unlike the prior art by use of adaptive temperature controller 10, any length or size of electrically-electrically conductive material 50 may be used for heating. Providing use of any length or size of material is of significance as dimensions of heating materials may vary due to fluctuations in materials and cutting techniques. Moreover, unlike the prior art, separate temperature sensors are unnecessary as temperature may be determined at any time by measurement of the voltage and current applied.

It is desirable that adaptive temperature controller 10 include a learning step to determine the responsiveness of the resistance, and therefore temperature, of electrically-conductive material 50 to change in current, voltage or power. Determination of responsiveness is important to reduce or eliminate overshoot and/or undershoot of temperature by adaptive temperature controller 110. Having determined the resistance of electrically-conductive material 50 at ambient temperature, adaptive temperature controller 10 may then determine the rate of temperature increase relative to an increase in voltage, current or power. An electrically-conductive material 50 having a large diameter will exhibit a lower rate of rise of temperature proportionate to increase in current, voltage or power. Likewise, an electrically-conductive material 50 having a small diameter will exhibit a high rate of rise of temperature proportionate to an increase in current, voltage or power. In each case, the change in temperature is also related to a known thermal coefficient of resistance for the material of which electrically-conductive material 50 is composed. For the range of operation the thermal coefficient of resistance may be assumed to be a constant. Adaptive temperature controller 10 therefore determines the resulting change in resistance incident to a burst of current, voltage or power applied to electrically-conductive material 50. Adaptive temperature controller 10 thereby avoids overshoot or undershoot of the desired temperature of temperature rate change by determining in advance the responsiveness of electrically-conductive material 50 to changes in current, voltage or power. In an alternative embodiment, adaptive temperature controller 10 may include a look-up table of known materials used for electrically-conductive material 50 at various temperatures and include the appropriate thermal coefficient of resistance at the temperature of electrically-conductive material 50 to determine the associated increase in temperature. In a further embodiment, adaptive temperature controller 10 may record the change in resistance as a function of the change in current throughout operation, thereby mapping the function throughout.

Adaptive temperature controller 10 may control or maintain one or more electrically conductive materials 50.

Further, adaptive temperature controller 10 may control an electrically-conductive material 50 to provide varying temperatures to a particular device or over a corresponding period of time, such as stepped or ramped temperature increases.

In a further embodiment, adaptive temperature controller 10 may be used in conjunction with a component 101 composed of an electrically-conductive material 50 such as nickel. Once the thermal coefficient of resistance of electrically-conductive material 50 is known, the temperature of component 101 may be controlled, such that the temperature may be increased at a stepped or fixed rate to provide increased separation between compounds having similar boiling points The adaptive temperature controller 10 configured to control the temperature of an electrically-conductive material 50 by determination of resistance and application of power, current or voltage provides several advantages over the prior art, particularly temperature controllers using heater cartridges. As no separate heater cartridge is required intermediate the heating element and the temperature controller, the mass of adaptive temperature controller 10 is less than that of such temperature controllers. Moreover, localized areas of increased or decreased temperature may be avoided as the heat flux is distributed over a large area, rather than emanating from a particular location associated with the heater cartridge. Further, the temperature may be more uniformly distributed since the heat is transferred from the surface along the length of the column 101 to provide an even distribution along its length rather than from one side associated with a cartridge heater. Finally temperature increases may be accomplished quite rapidly as the heat is generated within the electrically-conductive material 50 rather than transferred through a heat-conductive material from an exterior element.

Figure 4:
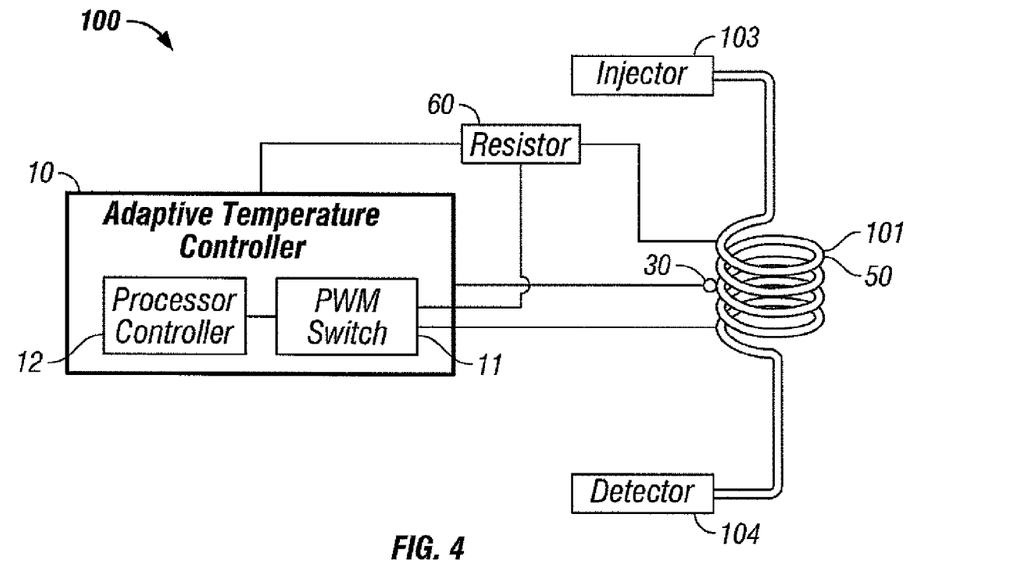
FIG. 4 depicts component 101 where heating is controlled by the adaptive temperature controller via a pulse-width-modulated switching supply controlled by a microcontroller/microprocessor.

As depicted in FIG. 4, in one embodiment, wherein component 101 is comprised of electrically-conductive material 50, power for producing heating is supplied by adaptive temperature controller 10 via a pulse-width-modulated switching supply 11 controlled by a microcontroller/microprocessor 12, although other supply control systems known in the art may alternatively be used. The current supplied to electrically-conductive material 50 is determined by detecting the voltage drop across a current-sense resistor 60, typically 0.1 Ohms, placed between the pulse-width modulated switching supply and electrically-conductive material 50. Likewise the voltage across electrically-conductive material 50 is detected. Amplifiers to properly scale the detected voltages may be used before the representative signals are passed to analog-to-digital converters. The digitized signals thereby obtained, e.g. at 1000 times per second, are passed to a microcontroller wherein the relative resistance value is obtained by application of Ohm's Law, namely by dividing the converted voltage value by the converted current value. The relative resistance value may be compared against a reference resistance value for temperature control employing the conventional proportional-integral-derivative (PD) control algorithm. The temperature of electrically-conductive material 50 may also be determined for display or recording by solving the equation relating temperature to resistance well known in the art or interpolating a value from a table.

For temperature ramping, the detected signal from the current-sense circuit may be used to control the rate, linear, exponential or otherwise, of temperature change by virtue of controlling for constant current within electrically-conductive material 50.

Figure 5:
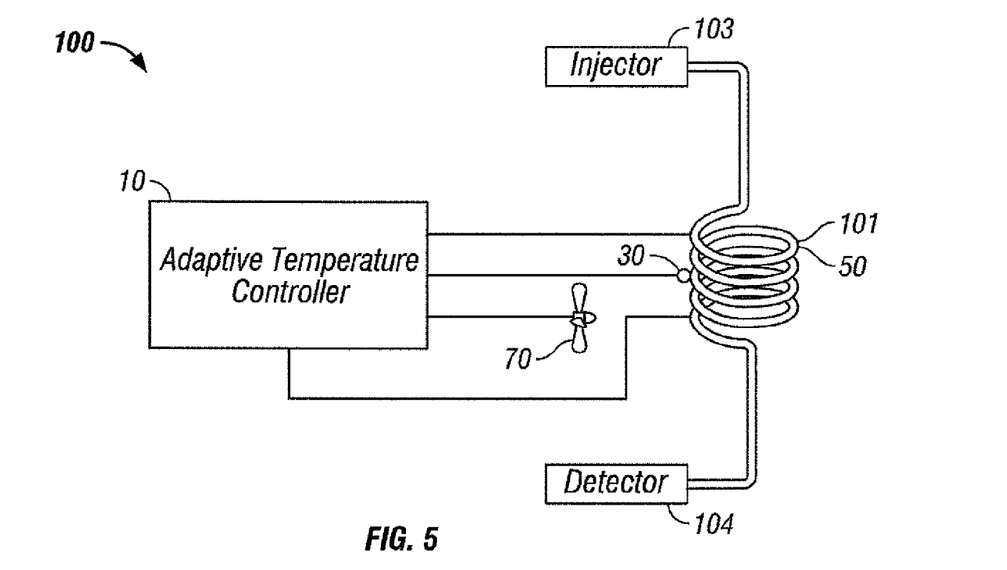
FIG. 5 depicts component 101 where heating and cooling is controlled by the adaptive temperature controller.

In a further embodiment, depicted in FIG. 5, an adaptive temperature controller 10 may be configured to control the temperature of electrically-conductive material 50 and a fan 70 which may induce air flow about component 101. Fan 70 may be used to increase the rate of cooling of electrically-conductive material 50.

Figure 6:
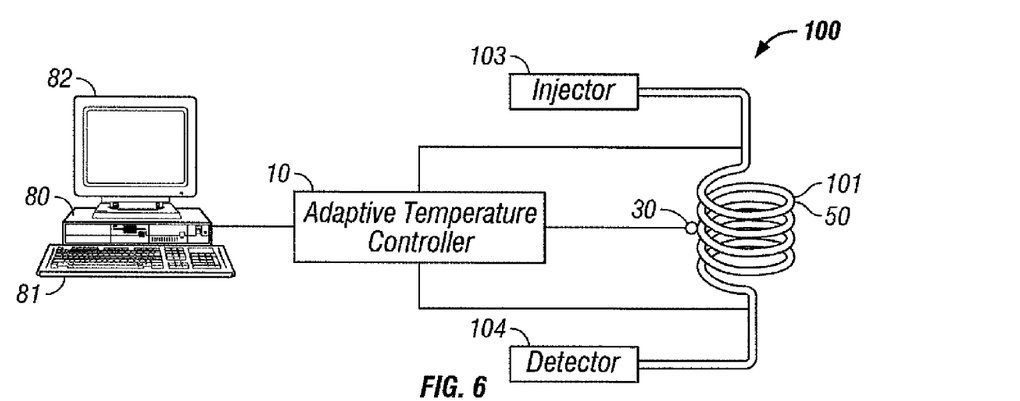
FIG. 6 depicts component 101 where heating is controlled by the adaptive temperature controller which includes a computer interface.
Figure 7:
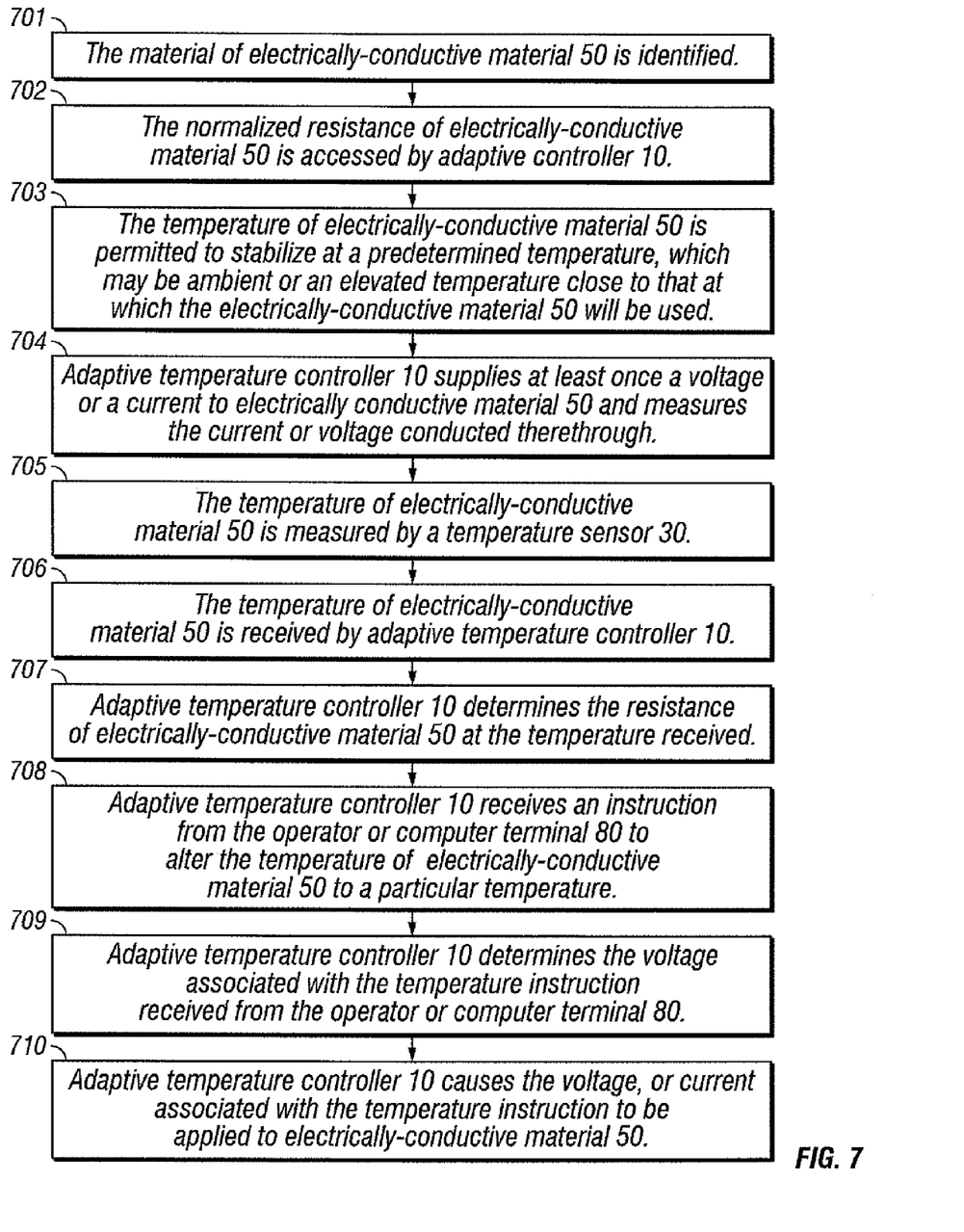
FIG. 7 depicts a flow diagram of one embodiment of the steps for calibration of the adaptive temperature controller with an electrically conductive material.

In a further embodiment, depicted in FIG. 6, adaptive temperature controller 10 includes a computer terminal 80. The computer terminal 80 provides an interface for control via a keyboard 81 and monitor 82. The computer terminal 80 may be any computer, including a conventional desktop computer or a handheld computer, such as those associated with Palm®, and electrically conductive material 50 calibration may be accomplished in the following steps, depicted in FIG. 7:

1) Step 701—The material of electrically-conductive material 50 is identified;

2) Step 702—The normalized resistance characteristic of electrically-conductive material 50 is accessed by adaptive temperature controller 10;

3) Step 703—The temperature of electrically-conductive material 50 is permitted to stabilize at a predetermined temperature, which may be ambient or an elevated temperature close to that at which the electrically-conductive material 50 will be used;

4) Step 704—Adaptive temperature controller 10 supplies at least once a voltage or a current to electrically-conductive material 50 and measures the current or voltage conducted therethrough;

5) Step 705—The temperature of electrically-conductive material 50 is measured by a temperature sensor 30;

6) Step 706—The temperature of electrically-conductive material 50 is received by adaptive temperature controller 10;

7) Step 707—Adaptive temperature controller 10 determines the resistance of electrically conductive material 50 at the temperature received;

8) Step 708—Adaptive temperature controller 10 receives an instruction from the operator or computer terminal 80 to alter the temperature of electrically-conductive material 50 to a particular temperature;

9) Step 709—Adaptive temperature controller 10 determines the voltage associated with the temperature instruction received from the operator or computer terminal 80;

10) Step 710—Adaptive temperature controller 10 causes the voltage, or current associated with the temperature instruction to be applied to electrically-conductive material 50.

Figure 8:
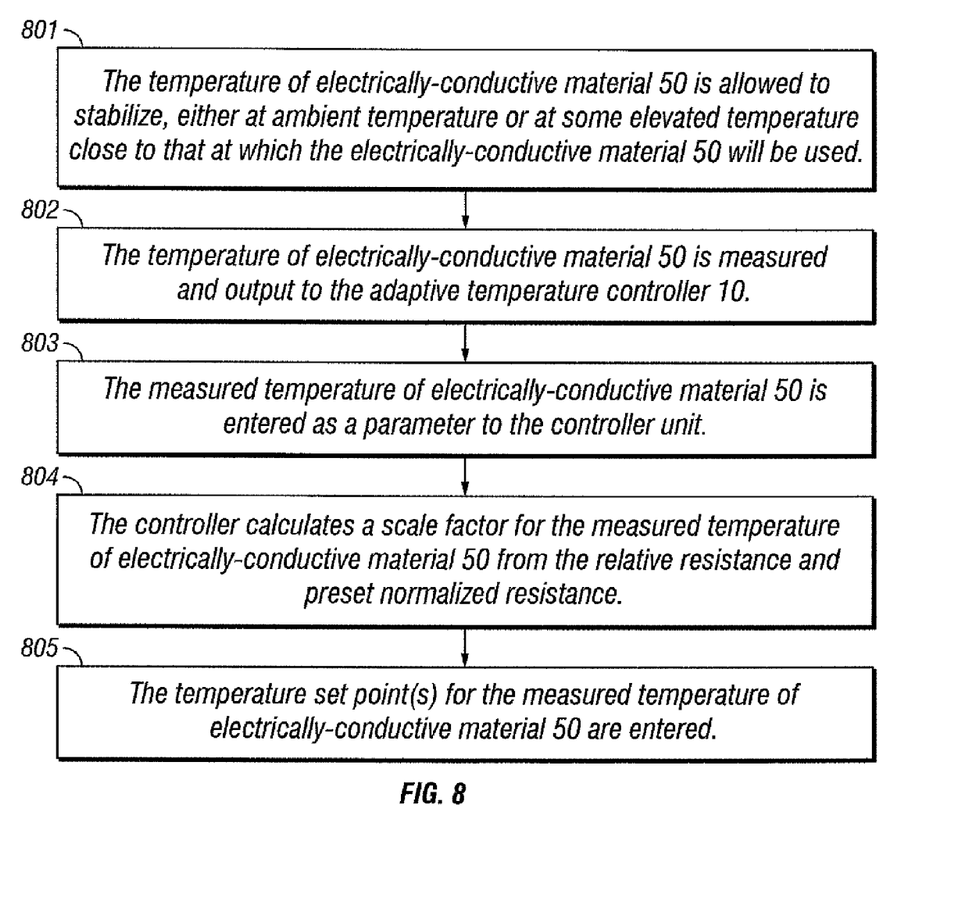
FIG. 8 depicts a flow diagram of an alternative embodiment of the steps for calibration of the adaptive temperature controller with an electrically conductive material.

Alternatively, as depicted in FIG. 8, calibration of the electrically-conductive material 50 may be accomplished in the following steps:

1) Step 801—The temperature of electrically-conductive material 50 is allowed to stabilize, either at ambient temperature or at some elevated temperature close to that at which the electrically-conductive material 50 will be used;

2) Step 802—The temperature of electrically-conductive material 50 is measured and output to the adaptive temperature controller 10;

3) Step 803—The measured temperature of electrically-conductive material 50 is entered as a parameter to the controller unit;

4) Step 804—The controller calculates a scale factor for the measured temperature of electrically-conductive material 50 from the relative resistance and preset normalized resistance characteristic; and 5) Step 805—The temperature setpoint(s) for the measured temperature of electrically-conductive material 50 are entered.

The terms and expressions which have been employed in the foregoing specification are used therein as terms of description and not of limitation, and there is no intention, in the use of such terms and expressions, of excluding equivalents of the features shown and described or portions thereof.

We claim:

1. An adaptive temperature controller for simultaneous temperature measurement and control for use with an electrically-conductive material to heat a system component, comprising:

a temperature sensor,
    said temperature sensor determining the temperature of said electrically-conductive material;
a device for measuring resistance,
    said device for measuring resistance recording measurement of two members of the group consisting of power, current and voltage;
    said device for measuring resistance determining resistance of said electrically-conductive material by application of Ohm's Law to said two members of the group consisting of power, current and voltage;
a power supply,
    said power supply in electrical communication with said electrically-conductive material
    said electrically-conductive material altering temperature based on said electrical communication from said power supply;
a device for controlling the output of said power supply,
    said device for measuring resistance outputting said determination of the resistance of said electrically-conductive material to said device for controlling the output of said power supply, said temperature sensor outputting the determination of the temperature of said electrically-conductive material to said device for controlling the output of said power supply;

said device for controlling the output of said power supply determining the thermal coefficient of resistance of said electrically-conductive material based on the output of said device for measuring resistance and the output of said temperature sensor;

said device for controlling the output of said power supply controlling the temperature of said electrically-conductive material based on the output of one of the group of power, voltage or current.

2. The adaptive temperature controller of claim 1 further comprising a pulse-width-modulated switching supply controlled by a microcontroller/microprocessor.

3. The adaptive temperature controller of claim 1 further comprising a fan to induce air flow about said component.

4. The adaptive temperature controller of claim 2 further comprising a fan to induce air flow about said component.

5. The adaptive temperature controller of claim 1 wherein said adaptive temperature controller communicates with a computer.

6. The adaptive temperature controller of claim 2 wherein said adaptive temperature controller communicates with a computer.

7. The adaptive temperature controller of claim 4 wherein said adaptive temperature controller communicates with a computer.

8. A method for calibrating an adaptive temperature controller for simultaneous temperature measurement and control for use with an electrically-conductive material to heat a system component, said adaptive temperature controller including:

a temperature sensor,
said temperature sensor determining the temperature of said electrically-conductive material;

a device for measuring resistance,
said device for measuring resistance recording measurement of two members of the group consisting of power, current and voltage;
said device for measuring resistance determining resistance of said electrically-conductive material by application of Ohm's Law to said two members of the group consisting of power, current and voltage;

a power supply,
said power supply in electrical communication with said electrically-conductive material
said electrically-conductive material altering temperature based on said electrical communication from said power supply;

a device for controlling the output of said power supply,
said device for measuring resistance outputting said determination of the resistance of said electrically-conductive material to said device for controlling the output of said power supply,
said temperature sensor outputting the determination of the temperature of said electrically-conductive material to said device for controlling the output of said power supply;
said device for controlling the output of said power supply determining the thermal coefficient of resistance of said electrically-conductive material based on the output of said device for measuring resistance and the output of said temperature sensor; and
said device for controlling the output of said power supply controlling the temperature of said electrically-conductive material based on the output of one of the group of power, voltage or current, comprising:
identifying the material of said electrically-conductive material;
said adaptive temperature controller accessing the normalized resistance of said electrically-conductive material;
permitting the temperature of electrically-conductive material to stabilize at a predetermined temperature;
said adaptive temperature controller supplying at least once a voltage or a current to electrically-conductive material and measuring the current or voltage conducted therethrough;
said temperature sensor measuring the temperature of electrically-conductive material;
said adaptive temperature controller receiving said temperature sensor measurement;
said adaptive temperature controller determining the resistance of electrically conductive material at said temperature sensor measurement;
said adaptive temperature controller receiving an instruction to alter the temperature of electrically-conductive material to a particular temperature;
said adaptive temperature controller determining the voltage associated with the temperature instruction received; and
said adaptive temperature controller causing one of the group of voltage and current associated with the temperature instruction to be applied to electrically-conductive material.

9. A method for calibrating an adaptive temperature controller for simultaneous temperature measurement and control for use with an electrically-conductive material to heat a system component, said adaptive temperature controller including:

a temperature sensor,
said temperature sensor determining the temperature of said electrically-conductive material;

a device for measuring resistance,
said device for measuring resistance recording measurement of two members of the group consisting of power, current and voltage;
said device for measuring resistance determining resistance of said electrically-conductive material by application of Ohm's Law to said two members of the group consisting of power, current and voltage;

a power supply,
said power supply in electrical communication with said electrically-conductive material
said electrically-conductive material altering temperature based on said electrical communication from said power supply;

a device for controlling the output of said power supply,
said device for measuring resistance outputting said determination of the resistance of said electrically-conductive material to said device for controlling the output of said power supply,
said temperature sensor outputting the determination of the temperature of said electrically-conductive material to said device for controlling the output of said power supply;
said device for controlling the output of said power supply determining the thermal coefficient of resistance of said electrically-conductive material based on the output of said device for measuring resistance and the output of said temperature sensor; and said device for controlling the output of said power supply controlling the temperature of said electrically-conductive material based on the output of one of the group of power, voltage or current, comprising:

allowing the temperature of said electrically-conductive material to stabilize;

measuring the temperature of said electrically-conductive material outputting the measurement of said temperature of said electrically-conductive material to said adaptive temperature controller;

entering said measurement of said temperature of said electrically-conductive material as a parameter to said adaptive temperature controller;

said adaptive temperature controller calculating a scale factor for said measurement of said temperature of said electrically-conductive material from a relative resistance and a preset normalized resistance characteristic; and entering into said adaptive temperature controller at least one temperature setpoint for said measurement of said temperature of said electrically-conductive material.

\* \* \* \* \*